United States Patent
Liu et al.

(10) Patent No.: US 11,730,439 B2
(45) Date of Patent: Aug. 22, 2023

(54) FAST 3D RADIOGRAPHY USING X-RAY FLEXIBLE CURVED PANEL DETECTOR WITH MOTION COMPENSATED MULTIPLE PULSED X-RAY SOURCES

(71) Applicants: Jianqiang Liu, Campbell, CA (US); Manat Maolinbay, Gilroy, CA (US); Chwen-yuan Ku, San Jose, CA (US); Linbo Yang, Pleasanton, CA (US)

(72) Inventors: Jianqiang Liu, Campbell, CA (US); Manat Maolinbay, Gilroy, CA (US); Chwen-yuan Ku, San Jose, CA (US); Linbo Yang, Pleasanton, CA (US)

(73) Assignee: AIXSCAN, Inc., Sunnyvale, CA (US)

( * ) Notice: Subject to any disclaimer, the term of this patent is extended or adjusted under 35 U.S.C. 154(b) by 103 days.

(21) Appl. No.: 17/506,507

(22) Filed: Oct. 20, 2021

(65) Prior Publication Data
US 2022/0313184 A1 Oct. 6, 2022

Related U.S. Application Data

(60) Provisional application No. 63/226,508, filed on Jul. 28, 2021, provisional application No. 63/225,194, (Continued)

(51) Int. Cl.
*A61B 6/00* (2006.01)
*A61B 6/02* (2006.01)
(Continued)

(52) U.S. Cl.
CPC .............. *A61B 6/541* (2013.01); *A61B 6/025* (2013.01); *A61B 6/032* (2013.01); *A61B 6/035* (2013.01);
(Continued)

(58) Field of Classification Search
CPC ........ A61B 6/4007; A61B 6/032; A61B 6/025
See application file for complete search history.

(56) References Cited

U.S. PATENT DOCUMENTS

| | | | |
|---|---|---|---|
| 2009/0080598 A1* | 3/2009 | Tashman | A61B 5/1038 378/11 |
| 2010/0172561 A1* | 7/2010 | Ota | G01N 23/046 378/19 |

(Continued)

*Primary Examiner* — Dani Fox
(74) *Attorney, Agent, or Firm* — Patent PC; Bao Tran

(57) ABSTRACT

An X-ray imaging system using multiple pulsed X-ray sources in motion to perform high efficient and ultrafast 3D radiography using an X-ray flexible curved panel detector is presented. There are multiple pulsed X-ray sources mounted on a structure in motion to form an array of sources. The sources move simultaneously relative to an object on a predefined arc track at a constant speed as a group. Each individual X-ray source can move around its static position at a small distance. When an individual source has a speed equal to group speed, but with opposite moving direction, the individual source and detector are activated. This allows source to stay relatively standstill during activation. The operation results in reduced source travel distance for each individual source. 3D radiography image data can be acquired with much wider sweep angle in much shorter time, and image analysis can also be done in real-time.

19 Claims, 4 Drawing Sheets

Related U.S. Application Data filed on Jul. 23, 2021, provisional application No. 63/224,521, filed on Jul. 22, 2021, provisional application No. 63/222,847, filed on Jul. 16, 2021, provisional application No. 63/220,924, filed on Jul. 12, 2021, provisional application No. 63/214,913, filed on Jun. 25, 2021, provisional application No. 63/209,498, filed on Jun. 11, 2021, provisional application No. 63/194,071, filed on May 27, 2021, provisional application No. 63/188,919, filed on May 14, 2021, provisional application No. 63/182,426, filed on Apr. 30, 2021, provisional application No. 63/175,952, filed on Apr. 16, 2021, provisional application No. 63/170,288, filed on Apr. 2, 2021.

(51) Int. Cl.

| | | |
|---|---|---|
| G06T 17/00 | (2006.01) | |
| G01N 23/044 | (2018.01) | |
| A61B 6/03 | (2006.01) | |
| A61B 6/06 | (2006.01) | |
| G01N 23/083 | (2018.01) | |
| G01N 23/18 | (2018.01) | |
| G06T 7/00 | (2017.01) | |
| G06T 11/00 | (2006.01) | |
| A61B 6/04 | (2006.01) | |
| G06T 7/11 | (2017.01) | |
| G16H 10/60 | (2018.01) | |
| G16H 30/20 | (2018.01) | |
| G16H 50/20 | (2018.01) | |
| G06V 10/25 | (2022.01) | |
| G06V 10/62 | (2022.01) | |
| A61B 6/08 | (2006.01) | |

(52) U.S. Cl.
CPC .............. *A61B 6/0407* (2013.01); *A61B 6/06* (2013.01); *A61B 6/08* (2013.01); *A61B 6/405* (2013.01); *A61B 6/4007* (2013.01); *A61B 6/4014* (2013.01); *A61B 6/4021* (2013.01); *A61B 6/4208* (2013.01); *A61B 6/4283* (2013.01); *A61B 6/4405* (2013.01); *A61B 6/4441* (2013.01); *A61B 6/4452* (2013.01); *A61B 6/4476* (2013.01); *A61B 6/4482* (2013.01); *A61B 6/467* (2013.01); *A61B 6/482* (2013.01); *A61B 6/54* (2013.01); *A61B 6/542* (2013.01); *A61B 6/56* (2013.01); *A61B 6/583* (2013.01); *G01N 23/044* (2018.02); *G01N 23/083* (2013.01); *G01N 23/18* (2013.01); *G06T 7/0012* (2013.01); *G06T 7/0016* (2013.01); *G06T 7/11* (2017.01); *G06T 11/003* (2013.01); *G06T 11/006* (2013.01); *G06T 17/00* (2013.01); *G06V 10/25* (2022.01); *G06V 10/62* (2022.01); *G16H 10/60* (2018.01); *G16H 30/20* (2018.01); *G16H 50/20* (2018.01); *A61B 6/4275* (2013.01); *A61B 6/502* (2013.01); *G01N 2223/401* (2013.01); *G06T 2200/24* (2013.01); *G06T 2207/10076* (2013.01); *G06T 2207/10081* (2013.01); *G06T 2207/20081* (2013.01); *G06T 2207/20084* (2013.01); *G06T 2207/30064* (2013.01); *G06T 2207/30096* (2013.01); *G06T 2207/30168* (2013.01); *G06T 2210/41* (2013.01); *G06V 2201/032* (2022.01)

(56) References Cited

U.S. PATENT DOCUMENTS

| | | | | |
|---|---|---|---|---|
| 2012/0076260 | A1* | 3/2012 | Kitagawa | G16H 30/40 382/128 |
| 2020/0345318 | A1* | 11/2020 | Turner | A61B 6/587 |

* cited by examiner

FAST 3D RADIOGRAPHY USING X-RAY FLEXIBLE CURVED PANEL DETECTOR WITH MOTION COMPENSATED MULTIPLE PULSED X-RAY SOURCES

The present invention claims priority to Provisional Application Ser. No. 63/182,426 filed on Apr. 30, 2021; 63/226,508 filed Jul. 28, 2021; 63/170,288 filed Apr. 2 2021, 63/175,952 filed Apr. 16, 2021, 63/194,071 filed May 27, 2021; 63/188,919 filed May 14, 2021; 63/225,194 filed Jul. 23, 2021; 63/209,498 filed Jun. 11, 2021; 63/214,913 filed Jun. 25, 2021; 63/220,924 filed Jul. 12, 2021; 63/222,847 filed Jul. 16, 2021; 63/224,521 filed Jul. 22, 2021; and U.S. application Ser. No. 17/149,133 filed Jan. 24, 2021, which in turn claims priority to Provisional Ser. 62/967,325 filed Jan. 29, 2020, the content of which is incorporated by reference.

FIELD OF THE INVENTION

This patent specification is in the field of 3D X-ray radiography systems and methods and particularly to using pulsed X-ray source and large field, digital flexible panel X-ray detectors.

BACKGROUND

There is one kind of digital X-ray 3D radiography like mammography; digital tomosynthesis (DTS) is a method for performing high-resolution limited-angle tomography at radiation dose levels comparable with conventional radiography. These digital tomosynthesis systems typically use an X-ray source mounted at one end of a rotatable assembly and a digital flat panel detector at the other. Between the x-ray source and the detector is a device that can compress and immobilize a breast. Compression of the breast is necessary for reduced X-ray to scatter, reduced radiation dose, more uniform optical density across the detector, and improved visualization of the anatomy. Tomosynthesis can be used to screen for early signs of breast cancer in women with no symptoms. This type of imaging can also be used as a diagnostic tool for women with breast cancer symptoms. Tomosynthesis is an advanced type of mammography. Digital Breast Tomosynthesis (DBT) detects more cancers and has fewer false-positive recalls and more precise lesion localization than 2D mammography. When tomosynthesis is performed, the X-ray source would need to move in an arc around the breast.

While the X-ray source moves around the breast, a series of low-dose X-ray images are acquired at different angles. The collected data set permits the reconstruction of parallel planes. Each plane is in focus, and those that are out-of-plane tissue images are blurred. Usually, a wider sweep angle would generate more data projections and result in better 3D resolution, but it takes longer. Data processing is manufacturer-specific because different reconstruction algorithms might be used. It should be emphasized that these kinds of digital tomosynthesis systems and methods can also be applied to other X-ray 3D radiography applications such as X-ray 3D chest diagnosis system for COVID, X-ray 3D Non-Destructive Test (NDT) system, and X-ray 3D security inspection system. There are prior arts with the single X-ray source and single flat panel to perform X-ray 3D radiography.

However, there are disadvantages among prior arts. The main disadvantage is that a single X-ray source takes a very long time to acquire good data projections. The second disadvantage is that it is difficult to do real-time reconstruction because the whole thing is too slow. The third disadvantage is that using a rigid X-ray flat panel detector has worse geometry distortion. Due to the fact that technology advances every day, electronics nowadays can be made flexible, faster, more compact, and more efficient. Just like a flexible solar panel charger, an X-ray detector can also be made flexible. A typical modern X-ray panel detector comprises a thin-film-transistor (TFT), a layer of X-ray scintillator, read-out electronics, etc. Although the read-out electronics board cannot be made flexible under current technology, the TFT-based detector can be flexible using a flexible substrate. The layer of scintillating material, or scintillator, such as Gd2O2S: Tb (GOS or GADOX), is already made to be somewhat flexible to attach to flexible film for X-ray imaging purposes decades ago.

SUMMARY

In the first aspect, a system to provide fast 3D radiography using multiple pulsed Xray sources in motion with a primary motor stage moving freely on an arc rail with a predetermined shape; a primary motor that engages with said primary motor stage and controls a speed of the primary motor stage; a plurality of secondary motor stages coupled to said primary motor stage and move along a direction of the arc rail; a plurality of secondary motors, each engaging a secondary motor stage and controlling a speed of secondary motor stage; a plurality of X-ray sources each moved by a secondary motor stage; a supporting frame structure that provides housing for the primary motor stage and secondary motor stages; and a flexible curved panel detector to receive X-ray imaging data.

In a second aspect, a method of fast 3D radiography using multiple pulsed X-ray sources in motion includes positioning a primary motor stage and one or more secondary motor stages to a predetermined initial location; sweeping the primary motor stage at a predetermined constant speed by said primary motor; oscillating each of the secondary motor stages by a corresponding secondary motor with a predetermined sequence; electrically activating an X-ray source and a flexible curved panel detector when a secondary motor stage moves in an opposite direction to that of the primary motor stage and at a selected speed of the primary motor stage; and acquiring image data from the X-ray source with a flexible curved panel detector.

In another aspect, an X-ray imaging system using multiple pulsed X-ray sources in motion to perform ultrafast, high efficient 3D radiography is presented. In the system, multiple pulsed X-ray sources are mounted on a structure in motion to form an array of the source. The multiple X-ray sources move simultaneously around an object on a predefined track at a constant speed of a group. Each individual X-ray source can also move rapidly around its static position of a small distance. When an individual X-ray source has a speed that equals to group speed but an opposite moving direction, the individual X-ray source is triggered through an external exposure control unit. This arrangement allows the X-ray source to stay relatively standstill during the X-ray pulse trigger exposure duration. Multiple X-ray sources result in a much-reduced source travel distance for individual X-ray sources. X-ray receptor is an X-ray flexible curved panel detector. 3D radiography image projection data can be acquired with an overall much wider sweep in a much shorter period. Image analysis can also be done in real-time while the scan goes.

In another aspect, an X-ray imaging system using multiple pulsed X-ray sources in motion to perform high efficient and ultrafast 3D radiography includes multiple pulsed X-ray sources mounted on a structure in motion to form an array of sources. The multiple X-ray sources move simultaneously relative to an object on a pre-defined arc track at a constant speed as a group. Each individual X-ray source can also move rapidly around its static position at a small distance. When an individual X-ray source has a speed that is equal to group speed but with opposite moving direction, the individual X-ray source and X-ray detector are activated through an external exposure control unit. This arrangement allows the X-ray source to stay relatively standstill during the X-ray source activation and X-ray detector exposure. X-ray receptor is an X-ray flexible curved panel detector. Multiple X-ray source in motion operation results in a much-reduced source travel distance for individual X-ray sources. 3D radiography image data can be acquired with an overall wider sweep angle in a much shorter time, and image analysis can also be done in real-time while the scan goes.

In another aspect, an X-ray flexible curved panel detector would make it possible to have a curved geometry to minimize distortion. In implementations, the X-ray can also be randomly activated from one of any sources in the array using a random-firing scheme. Results of each and accumulated analysis determine the next X-ray source and exposure condition. 3D X-ray radiography images are reconstructed based on each image with an angled geometry of the X-ray exposure source. Much broader applications include 3D mammography or Tomosynthesis, chest 3D radiography for COVID or fast 3D NDT, fast 3D X-ray security inspection.

Advantages of the above systems may include one or more of the following. The various embodiments of multiple X-ray sources in motion are used in a novel ultrafast five 3D radiography system. The first advantage is that system overall is several times faster. Each x-ray source would only need to mechanically travel a small fraction of the whole distance in an arc trajectory. It greatly reduces the amount of data acquisition time needed for a patient at the X-ray diagnosis machine. The second advantage is that image analysis can also be done in real-time as the scan goes. Judgment on the images taken will have an impact on the X-ray source position for the next shot. There is no need to wait until the finish of the whole image acquisition to do layered image reconstruction. The third advantage is that acquiring high resolution and high contrast images is possible due to the reduction of motion artifacts. Each X-ray source is also mounted on a substructure that vibrates the source around its origin. The composition of vibration speed and track speed leads to the relative standstill position of the X-ray sources when the individual X-ray source is activated. The fourth advantage is that the system can go a much wider sweep to acquire more data projections faster. More data projections mean better image construction that would lead to a reduced misdiagnosis rate. The fifth advantage is that because of a wider angle and faster imaging acquisition. It is possible to add time components to 3D spatial imaging to form a 4D imaging data set. The sixth advantage is that X-ray flexible curved panel detector geometry will make much less image distortion.

The present invention has been described in terms of the preferred embodiment, and it is recognized that equivalents, alternatives, and modifications, aside from those expressly stated, are possible and within the scope of the appending claims.

BRIEF DESCRIPTION

DETAILED DESCRIPTION

Figure 1:
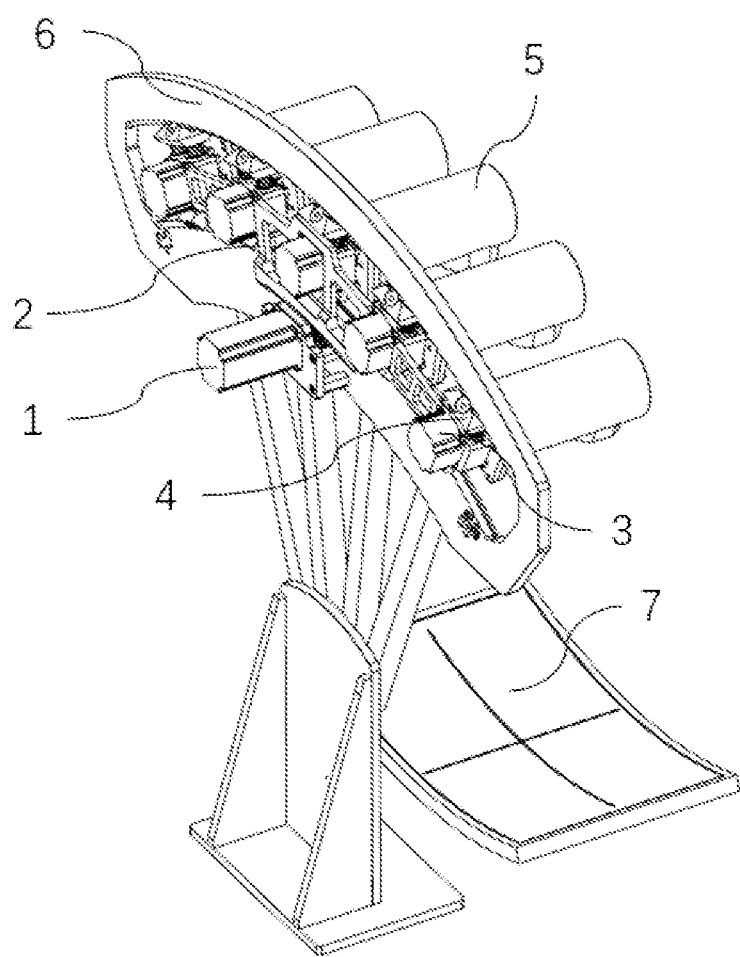
FIG. 1 illustrates an ultrafast 3D digital radiography system with multiple X-ray sources in motion using an X-ray flexible curved panel detector.

This invention will now be described more fully hereinafter with reference to the accompanying drawings, which show exemplary embodiments. Various embodiments are now described in reference to the drawings, wherein reference numerals refer to such elements throughout. In the following description, for purposes of explanation, numerous specific details are set forth in order to provide a thorough understanding of one or more embodiments. However, it may be evident that such embodiment(s) may be practiced without these specific details. In other instances, well-known structures and devices are shown in block diagram form in order to facilitate describing one or more embodiments.

Thus, for example, it will be appreciated by those of ordinary skill in the art that the diagrams, schematics, illustrations, and such as represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular named manufacturer.

FIG. 1 illustrates an ultrafast 3D digital radiography system using an X-ray flexible curved panel detector 7 with multiple X-ray sources 5 in motion. A primary motor 1 engaged with a primary motor stage 2 on which there are secondary motors 3, secondary motor stages 4 and multiple X-ray sources 5. All motors, all motor stages, and X-ray sources 5 are mounted in a supporting frame structure 6. Each secondary motor 3 is engaged to a secondary motor stage 4. All secondary motor stages 4 are mounted on a primary motor stage 2. Every X-ray source 5 is mounted on a secondary motor stage 4. Every motor is controlled by programmable motion control hardware and can move the motor stage back and forth at a predetermined speed. The secondary motor stages 4 are positioned in such a way that spacing to adjacent stages is equal. As a result, all X-ray source 5 moves together with the primary motor stage 2, but each individual X-ray source 5 can move individually with the secondary motor stage 4. The X-ray flexible curved panel detector 7 can be mounted on an additional linear stage. The X-ray flexible curved panel detector 7 can also move back and forth, based on the location of X-ray sources 5 to have a broader coverage of images.

A primary motor 1 with a travel encoder and position control system may be mounted on a frame structure 6 to provide movement along an arc rail that can have any predetermined shape. One or more secondary motors 3 coupled to the primary motor 1 through couplings and rotatable about their axis are positioned around the primary motor 1 and engage the primary motor stage 2 to drive the secondary motor stage 4. A plurality of X-ray sources 5 may be mounted on the secondary motor stage 4 and driven by the secondary motors 3 to move along the arc rail with the primary motor 1. The X-ray sources 5 may be activated through an external exposure control unit connected to the secondary motors 3. An X-ray flexible curved panel detector 7 may be used for the X-ray receptor in an embodiment. The primary motor 1 may be mounted on a motorized stage with a travel encoder and position control system and is operated by a primary motor controller to sweep around the arc rail with a constant speed in one direction.

A primary motor stage 2 provides a translation motion for the X-ray sources 5. The secondary motor stages 4 provide the oscillation left or right movement to each individual X-ray source 5. 3D image reconstruction based on iterative approach each individual X-ray source 5 generates a 3D data set which contains all the projections along an arc segment. Since there are multiple X-ray sources 5, it is possible to acquire projection data with a wider sweep than just one single X-ray source can achieve. X-ray data in different fields and views are very much sensitive to distortions due to inhomogeneity in X-ray absorption by different parts of body tissue. All images can be acquired under similar conditions of the object being imaged to form good image reconstruction data. The sweep angle between the individual images is very small to ensure consistent quality across all imaging data. The whole image acquisition process of the present invention uses motion-compensated image processing technology.

The primary motor stage 2 is coupled to the primary motor 1 with a planetary gear mounted on a structure in motion along an arc trajectory defined by rails. The X-ray sources move at the same speed as a group initially, and each individual X-ray source 5 can also move rapidly around its static position of a small distance. The number of X-ray sources 5 mounted on the structure is for illustration purposes only. There may be more or less than five sources depending on implementation. Secondary motor stages 4 are coupled to the secondary motor 3. Each secondary motor stage 4 moves in a back-and-forth direction of movement of the primary motor stage 2 along the arc trajectory of the rail. The X-ray sources 5 are moving at a predetermined speed relative to the object. The transmission of the X-rays through the object results in a projection data set, which can be used to form an image of the object.

A plurality of X-ray sources 5 is each mounted on the secondary motor stage 4. The X-ray sources 5 are triggered by programmed sequence, with each being turned on in sequence by an external exposure control unit. When the speed of the secondary motor stage 4 is substantially equal to that of the primary motor stage 2, an active individual X-ray source can remain relatively standstill during the X-ray pulse trigger exposure duration. In another aspect, an X-ray flexible curved panel detector 7 can be attached to the outer surface of the rigid structure. Each of the plurality of X-ray sources 5 will sequentially be activated for a period during which they send out X-rays through the object that are detected by the X-ray flexible curved panel detector 7.

Multiple X-ray sources 5 on an array move at a constant speed with different moving directions relative to an object. Each individual X-ray source can also move rapidly around its static position of a small distance when an individual X-ray source has a speed that equals to group speed but an opposite moving direction. The individual X-ray source is triggered through an external exposure control unit. This arrangement allows the X-ray source to stay relatively standstill during the X-ray pulse trigger exposure duration. Multiple X-ray sources result in a much-reduced source travel distance for individual X-ray sources. 3D radiography image data can be acquired with an overall wider sweep angle in a much shorter time, and image analysis can also be done in real-time. While the scan goes in the above system, the 3D X-ray receptor is an X-ray flexible curved panel detector 7, making it possible to have a curved geometry to minimize distortion. The 3D X-ray receptor detects X-ray images projected from a variety of X-ray sources 5.

A supporting frame structure 6 can be used to support and hold the primary motor stage 2, a plurality of secondary motor stages 4, an X-ray sources 5 in relative position. Each of the secondary motor stages 4 can be driven by a corresponding secondary motor 3 which is in turn driven by a d power source. The supporting frame structure 6 may be a tubular framework or a rectangular parallelepiped frame having enough space for the primary motor stages 2, the secondary motor stages 4, and the X-ray sources 5. The primary motor stage 2 can be driven by a corresponding primary motor 1 which is in turn driven by a power source. The primary motor 1 can engage with the primary motor stage 2 such that when it rotates, the primary motor stage 2 is also rotated. In some embodiments, the primary motor 1 may rotate at a constant speed, while the secondary motor 3 may rotate at different speeds based on the various movement instructions provided by the user. The supporting frame structure 6 may have sufficient mechanical strength and stiffness to provide structural support for the system.

An X-ray flexible curved panel detector 7 receives X-ray flux from an array of X-ray sources 5 arranged in motion to perform ultrafast, high efficient 3D radiography. In this system, there are multiple pulsed X-ray sources 5 mounted on a structure in motion to form an array of the source. The multiple X-ray sources 5 move simultaneously around an object on a pre-defined track at a constant speed of a group. Each individual X-ray source can also move rapidly around its static position of a small distance. When an individual X-ray source has a speed that equals to group speed but an opposite moving direction, the individual X-ray source 5 an X-ray flexible curved panel detector 7 are triggered through an external exposure control unit. This arrangement allows the X-ray source 5 to stay relatively standstill during the X-ray pulse trigger exposure duration to keep image sharp. Multiple X-ray sources 5 result in a much-reduced source travel distance for individual X-ray sources 5.

Figure 2:
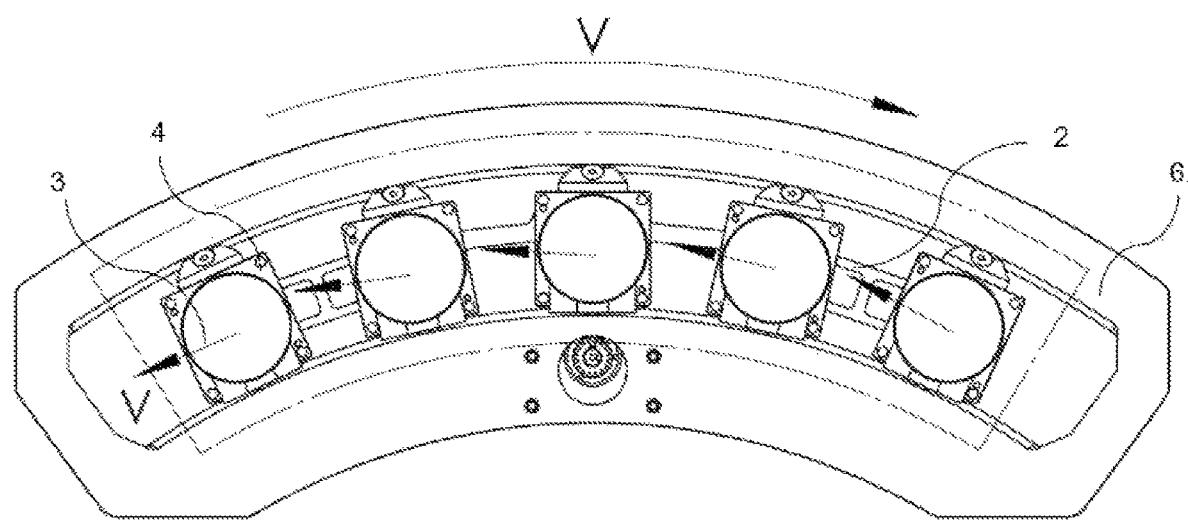
FIG. 2 illustrates an example where an individual X-ray source emits an X-ray beam in a momentary standstill position when the primary and secondary motor stages are moving in the opposite direction but with the same speed.

FIG. 2 illustrates that an individual X-ray source emits an X-ray beam in a momentary standstill position at the moment when the primary motor stage 2 and secondary motor stages 4 are moving in the opposite direction but with the same speed. For one data acquisition cycle, Primary motor stage 2 moves in one direction at a constant speed, then go back to the initial position. While primary motor stage 2 is moving at a constant speed, each secondary motor stage 4 is vibrating at the predetermined speed. When secondary motor stage 4 travels in the opposite direction to the primary motor stage 1 and has the same constant speed, X-ray source 5 and X-ray flexible curved panel detector 7 are triggered. At this moment of a trigger, an X-ray source 5 behaves like the X-ray source 5 is standstill while emitting an X-ray beam. Therefore, the dynamic arrangement of stationary state an X-ray source 5 allows an X-ray imaging system to acquire a large number of images from different spatial angle locations in a very short amount of time. Duration of constant speed motion of a secondary motor stage 4 can be programmed by software to match X-ray exposure time. When one secondary motor stage 4 is at the constant speed, the other secondary motor stage 4 could be in acceleration, deceleration, or move back to the initial position in order to get ready for their next constant speed. An X-ray source 5 can also be programmed to perform exposure on-demand based on each independent external trigger pulse in a random sequence. In view of the widely available superfast computer, image analysis can be done in real-time with image acquisition. Judgment on the images taken will impact the X-ray source 5 positions for the next shot. There is no need to wait until the finish of the whole image acquisition to do image reconstruction.

Primary motor stage 2 moves on an arc rail, with one or more secondary motor stages 4, an array of pulsed X-ray sources 5 is used to perform ultrafast, highly efficient dimensional 3D radiography. This concept works by moving the whole structure on a predetermined arc track at a constant speed of group. A group could be made up of one or more secondary motor stages 4 with an array of pulsed X-ray sources 5 attached to it. Each individual X-ray source 5 can also move rapidly around its static position of a small distance with speeds that are proportional to the group speed. When an individual X-ray source 5 has a speed that equals to group speed but an opposite moving direction, the individual X-ray source 5 is triggered through an external exposure control unit. This arrangement allows the X-ray source 5 to stay relatively standstill during the X-ray pulse trigger exposure duration. Multiple X-ray sources 5 result in a much-reduced source travel distance for individual X-ray sources 5. The array of pulsed X-ray sources 5 will produce a set of projection data sets. An X-ray detector is a flexible curved panel detector 7, its curvature can be changed on-site based on application need. X-ray receptor is an X-ray flexible curved panel detector 7. 3D radiography image projection data can be acquired with an overall much wider sweep in a much shorter period. Image analysis can also be done in real-time while the scan goes.

Secondary motor 3 at this time would start moving along the direction of primary motor movement. X-ray sources 5 will start radiating X-rays, and at the same time, X-ray receptors would receive the X-ray imaging data or charge packets generated by the radiations. At the end of primary motor 1 movement the primary motor starts rotating back toward its starting position. The secondary motor 3 also starts moving back to its original location after the X-ray source 5 has finished radiating X-rays.

One or more secondary motor stages 4 are mounted on the structure for each array of X-ray sources 5. Each of the secondary motor stages 4 is designed to move its associated X-ray source 5 with a predetermined sequence. The pre-defined sequence can sweep the associated X-ray source 5 around an arc track with a predetermined shape at a constant speed of the group. The secondary motor stage 4 can also move its associated X-ray source 5 fast around its static position at a small distance relative to its initial location. A speed control unit that allows independent control of the speed of the secondary motor stages 4; is coupled to each of the secondary motor stages 4. This provides an ability to control the speed of the secondary motor stages 4.

X-ray in motion with the group will be triggered only when it has a speed that equals to group speed but opposite moving direction. Each individual X-ray source can also move rapidly around its static position of a small distance, when there is no opposite movement by another X-ray source 5. When an individual X-ray source 5 has a speed that equals to group speed but opposite moving direction, the individual X-ray source 5 and X-ray flexible curved panel detector 7 are activated through an external exposure control unit. This arrangement allows the X-ray source 5 to stay relatively standstill during the X-ray pulse trigger exposure duration. A primary motor stage 2 and one or more secondary motor stages 4 will be positioned to a predetermined initial location. The primary motor 1 will sweep the primary motor stage 2 at a predetermined constant speed. The primary motor stage 2 and the secondary motor stages 4 will be coupled to each other by gears or belts or other linkages such as chains, cables, ropes, etc. One or more individual pulsed X-ray sources 5 will be mounted on a structure in motion to form an array of sources. The multiple X-ray sources 5 move simultaneously relative to an object on a pre-defined arc track at a constant speed as a group. Each individual X-ray source 5 can also move rapidly around its static position at a small distance.

X-ray flexible curved panel detector 7 is a new form of X-ray detector where it is much thinner than a traditional X-ray film plate. It also is very flexible and can easily curve into many different curvature. For example, in some embodiments, the detector can even be curved into a circle shape to acquire images around a human chest. Its geometry distortion is minimal and very sensitive. This combination makes it suitable for mammography or 3D X-ray security inspection since multiple sources are used at the same time. The detector could be placed at the center position in the array and detect all sources simultaneously. The large array of sources allows random firing schemes to reduce exposure time per source while achieving an overall high image quality. X-ray flexible curved panel detector 7 with varying pixel size is a new type of X-ray detector that includes variable pixel sizes by binnings. This will enable a single detector to provide sufficient data resolution in various applications.

Figure 3:
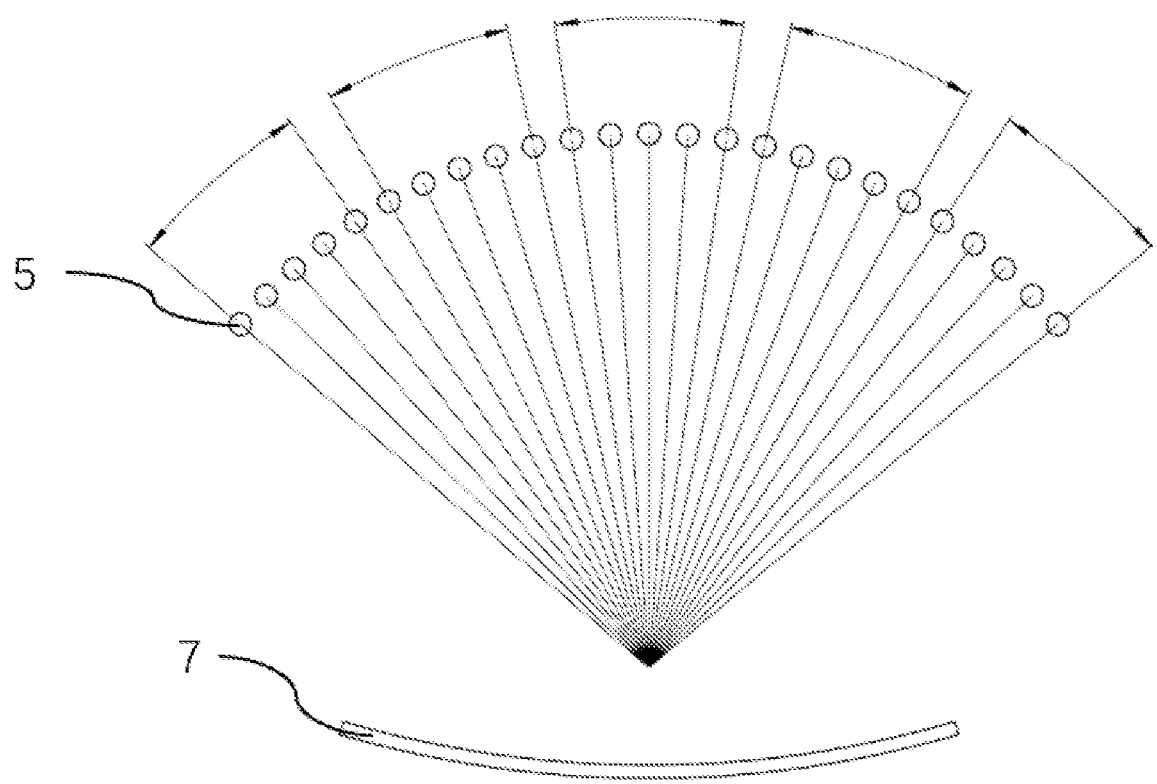
FIG. 3 illustrates an exemplary configuration where a five-X-ray-source system takes 25 sets of projection data by each traveling only one-fifth of the total distance using an X-ray flexible curved panel detector.

FIG. 3 illustrates a complete exposure position. In this case, there are five X-ray sources 5, and the five X-ray sources 5 perform 25 total X-ray exposures at different angle positions. But each secondary motor stage 4 only needs to travel one-fifth of the total travel distance. Therefore, with multiple X-ray sources 5 working in parallel, a large amount of projection data can be acquired at a fraction of the amount of time. X-ray flexible curved panel detector 7 is an X-ray receiver. The total number of total X-ray sources 5, in this case, is five for one set. In practice, the total number of X-ray sources 5 can be from two to even eight or more for one set. Electronic signals always go faster than that mechanical motion. A bottleneck of limiting factor is always motor stage motion itself. The next bottleneck is the detector readout limitations. Because detector also needs some time to read out many megapixel data and then transfer to a computer.

X-ray sources 5 are mounted on a structure in motion to form an array of sources. Each X-ray source 5 can also move rapidly around its static position at a small distance when an individual X-ray source 5 has a speed equal to group speed but opposite moving direction. The individual X-ray source 5 and X-ray flexible curved panel detector 7 are activated through an external exposure control unit. This arrangement allows the X-ray source 5 to stay relatively standstill during the X-ray pulse trigger exposure duration. Multiple X-ray sources result in a much-reduced source travel distance for individual X-ray sources 5. X-ray receptor is an X-ray flexible curved panel detector 7. 3D radiography image data can be acquired with an overall much wider sweep in a much shorter time, and image analysis can also be done in real-time while the scan goes. X-ray detectors, as an example of imaging receptors, are very flexible due to the nature of substrate materials, therefore allowing more robustness to some unwanted influences such as vibration shock, strong magnetic field, etc. The X-ray flexible curved panel detectors 7 are usually formed by one single continuous material.

X-ray flexible curved panel detector 7 is coupled to an X-ray source 5 through high voltage cables, and a flexible cable connects the X-ray source 5 to an exposure control unit that provides trigger signals to the source. Similarly, flexible cable couples X-ray detector to an acquisition control unit that generates exposure and timing signals to detect multiple X-ray sources 5 and detectors mounted on a structure and moved along arc rail at a constant group speed. The X-ray source 5 has a typical peak power and produces a pulse beam with average power. Each detector typically collects large amount of data during one pulse wide. The detector signal processing unit converts signals from each detector into digital image data using common 3D X-ray detector systems methods known in the art. This fast 3D radiography technique and equipment provide both wide-angle coverage and fast imaging.

Figure 4:
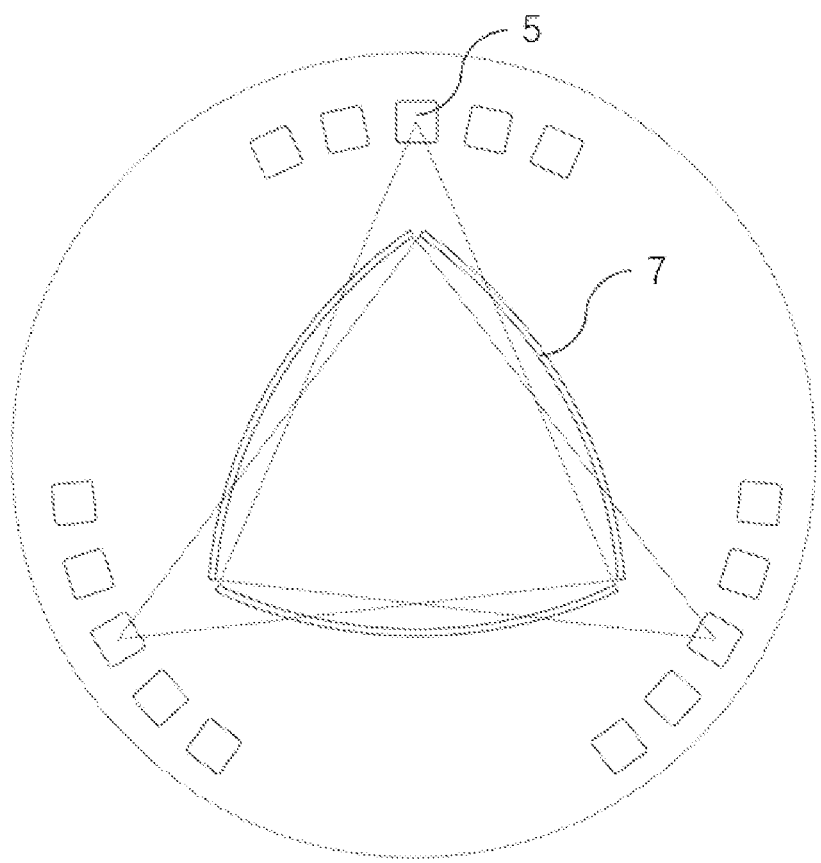
FIG. 4 illustrates an exemplary configuration of combined three sets of the independent systems that can be used in parallel to cover much larger X-ray scan angles.

FIG. 4 illustrates a configuration of three sets of an independent X-ray imaging system that can be used in parallel as a combo to cover more sweep angles. If sweep angle coverage of each individual set is relatively small, say less than 100 degrees, then three sets can be in the same plane to cover close to 360 degrees. However, in a three-set combo configuration, three sets do not have to be in the same plane. In addition to one set and three set combos, two set combo can also be used in practice. One advantage of two sets configuration is that most likely, they are in the same plane. The invention has been described in detail with particular reference to a presently preferred embodiment. Still, it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The flexible curved panel detector 7 includes a light-receiving area that has a curved surface to form a curved geometry. A gantry supports an X-ray source 5 at one end of the detector and moves it on an arc trajectory relative to a sample under examination. The sample may be a human body part or an object like an electronic device part, for example. A fixed motor-driven detector table can be also mounted behind the detector. An array of multiple X-ray sources 5 is supported by a structure that can move it simultaneously in the opposite direction to that of a motor-driven X-ray source table. The X-ray sources 5 in motion include five sources indicated by numerals. Sources are each spaced apart by degrees in a semi-circle around the arc rail. The source is spaced apart from source degrees. Each of the sources is coupled to a corresponding controller so that when a source has a speed that equals to group speed but with opposite moving direction, it will be triggered to emit X-rays.

Sweep angle and radius may vary. The radius of the arc path determines maximum object size. It can also be measured in terms of track length or time for complete movement. Each of the X-ray sources 5 has its motion control system. Multiple motion systems, one for each X-ray source 5, can be configured to move simultaneously around an object on a pre-defined track at a constant speed of a group. The individual X-ray sources 5 can also move rapidly around its static position of a small distance. When an individual X-ray source 5 has a speed that equals to group speed but an opposite moving direction, the individual X-ray source 5 is triggered through an external exposure control unit. This arrangement allows the X-ray source 5 to stay relatively standstill during the X-ray pulse trigger exposure duration. Each of the X-ray sources 5 is controlled by their respective independent motion control systems. A panel detector structure provides detection for multiple pulsed X-ray sources 5 in motion operation. For example, the flexible curved panel detector or another type of X-ray detector. An X-ray flexible curved panel detector 7 would make it possible to have a curved geometry to minimize image distortion.

The present invention relates to ultrafast 3D X-ray imaging and can be used in different fields, such as medical diagnosis, industrial process inspection, transportation safety inspection, X-ray security inspection, etc. This patent also provides a number of embodiments. In a first embodiment, a 3D X-ray imaging system using multiple pulsed X-ray sources in motion with a primary motor stage moving freely on an arc rail with a predetermined shape includes a primary motor that engages with said primary motor stage 2 and controls a speed of the primary motor stage 2; a plurality of secondary motor stages 4 coupled to said primary motor stage 2 and move along a direction of the arc rail; a plurality of secondary motors 3, each engaging a secondary motor stage 4 and controlling a speed of secondary motor stage 4; a plurality of X-ray sources 5 each moved by a secondary motor stage 4; a supporting frame structure 6 that provides housing for the primary motor stage 1 and secondary motor stages 4; and an X-ray flexible curved panel detector 7 to receive X-ray flux to generate imaging data.

A primary motor 1 that engages with said primary motor stage 2 and controls a speed of the primary motor stage 2, wherein a structure is movably coupled to the primary motor stage 2 and couples with a secondary motor stage 4. One embodiment of the present invention uses an array of X-ray sources 5 to provide fast 3D-dimensional radiography images by moving each X-ray source 5 on a pre-defined track. The main drive structure is used to move one or more X-ray sources 5 in two orthogonal directions at the same time while scanning objects. The X-ray sources 5 may move around the object in opposite directions, wherein when one X-ray source 5 moves in one direction, another X-ray source 5 moves in the opposite direction. Multiple motors are controlling individual motors to control individual motion for each X-ray source 5. Each X-ray source 5 moves at the same speed as other X-ray sources 5 but at a different time frame. Each X-ray source 5 may also move rapidly around its static position of a small distance, wherein when an individual X-ray source 5 has a speed that equals to group speed but an opposite moving direction, the individual X-ray source 5 is triggered through an external exposure control unit. This arrangement allows the X-ray source 5 to stay relatively standstill during the X-ray pulse trigger exposure duration. The flexible curved panel detector will make it possible to have a curved geometry to minimize distortion.

A first embodiment of the invention includes a system to provide fast dimensional 3D radiography using multiple pulsed X-ray sources in motion with a primary motor stage moving freely on an arc rail with a predetermined shape; a primary motor 1 that engages with said primary motor stage 2 and controls a speed of the primary motor stage 2; a plurality of secondary motor stages 4 coupled to said primary motor stage 2 and move along a direction of the arc rail; a plurality of secondary motors 3, each engaging a secondary motor stage 4 and controlling a speed of secondary motor stage 4; a plurality of X-ray sources 5 each moved by a secondary motor stage 4; a supporting frame structure 6 that provides housing for the primary motor stage 2 and secondary motor stages 4; and an X-ray flexible curved panel detector 7 to receive X-ray flux to produce imaging data.

Primary motor 1 moves the primary motor stage 2. A plurality of secondary motors 3 engages a secondary motor stage 4, each controlling the speed of the secondary motor stage 4. Secondary motor stages 4 have a set of secondary motors 3 that control them to move along the direction of the arc rail. Each secondary motor stage 4 may have one or more X-ray sources 5 mounted on it. The X-ray flexible curved panel detector 7 receives X-ray flux from a plurality of X-ray sources 5 moving simultaneously around an object on a pre-defined track at a constant speed of a group. Each individual X-ray source 5 can also move rapidly around its static position of a small distance. When an individual X-ray source 5 has a speed that equals to group speed but an opposite moving direction, the individual X-ray source 5 is triggered through an external exposure control unit. This arrangement allows the X-ray source 5 to stay momentary standstill during the X-ray pulse trigger exposure duration.

The supporting frame structure 6 is detailed next. It consists of three sets of mounting brackets, namely a primary motor stage set, a secondary motor stage set, and a detector set. The primary motor stage set supports one or more motor secondary stages mounted on one or more X-ray sources 5. Primary motor stage has its motor, and it moves along the arc rail by engaging with the rail and is controlled by the speed of the primary motor. The motor could be an electrical stepper motor or servo motor etc. One or more secondary motor stages 4 support each X-ray source 5 and move along the direction of the arc rail. There could be several pairs of secondary motor stages 4 for each primary motor stage 2 to allow simultaneous movement of the primary motor stage 2 and its associated secondary motor stages 4. At least one flexible curved panel detector 7 (X-ray receptor) is mounted on a detector stage and receives X-ray flux. A first drive unit and a second drive unit drive the first and second motor stages, respectively. The first drive unit includes a first gearbox connected to the primary motor stage set and a first-speed control module connected to the first gearbox.

The present invention is described in terms of an ultrafast, high efficient dimensional 3D radiography system with multiple pulsed X-ray sources 5 moving at a constant speed. Multiple pulsed X-ray sources 5 are mounted on a structure in motion to form an array of the source. The array moves along a predetermined arc track while sweeping the object with an overall wide angle of view. Each individual X-ray source 5 can also move rapidly around its static position. When an individual X-ray source 5 has a speed that equals to group speed but opposite moving direction, the individual X-ray source 5 is triggered through an external exposure control unit. This arrangement allows the X-ray source 5 to stay relatively standstill during the X-ray pulse trigger exposure duration. Image data are acquired from the X-ray source 5 with an X-ray flexible curved panel detector 7. Data acquisition of 3D projection data takes place when the secondary motor stage 4 moves in an opposite direction to that of the primary motor stage 2 and at a selected speed of the primary motor stage 2. This arrangement allows the X-ray source 5 to stay relatively standstill during the X-ray pulse trigger exposure duration.

The description will focus on a system and method to perform fast dimensional X-ray imaging, but the techniques and devices may be applied to other applications, for example, in mammography or other forms of dimensional imaging using x-rays, such as an X-ray flexible curved panel detector 7. One embodiment involves multiple pulsed X-ray sources 5 mounted on a structure in motion to form an array of X-ray sources 5. The multiple X-ray sources move simultaneously relative to an object on a pre-defined arc track at a constant speed as a group. Each individual X-ray source 5 can also move rapidly around its static position at a small distance. When an individual X-ray source 5 has a speed that is equal to group speed but with opposite moving direction, the individual X-ray source 5 and X-ray flexible curved detector 7 are activated through an external exposure control unit. This arrangement allows the X-ray source 5 to stay relatively standstill during the X-ray source 5 activation and X-ray detector exposure. A further embodiment of the present invention includes an X-ray flexible curved panel detector 7 for detecting X-ray photons emitted from an X-ray source 5 positioned on a structure that moves with respect to an object being imaged, where the flexible curved panel detector 7 includes a front surface with X-ray scintillator that receives the X-ray photons.

Sweeping the primary motor stage 2 is performed by engaging a primary motor 1 with a primary motor stage 2 and then rotating said primary motor 1 to engage with a predetermined number of gears and shafts to provide for free movement of the said primary motor stage 2 an arc rail with a predetermined shape. The method further includes sweeping the primary motor stage 2 at a predetermined constant speed by said primary motor 1.

Multiple X-ray sources 5 in motion simultaneously around an object on a pre-defined track at a constant speed of a group Three of the present inventions have been described in this patent application, namely systems and methods of fast 3D radiography using multiple pulsed X-ray sources 5 in motion with a primary motor stage 2 moving freely on an arc rail with a predetermined shape; a primary motor 1 that engages with said primary motor stage 2 and controls a speed of the primary motor stage 2; a plurality of secondary motor stages 4 coupled to said primary motor stage 2 and move along a direction of the arc rail; a plurality of secondary motors 3, each engaging a secondary motor stage 4 and controlling a speed of secondary motor stage 4; a plurality of X-ray sources each moved by a secondary motor stage 4; a supporting frame structure 6 that provides housing for the primary motor stage 2 and secondary motor stages 4; and an X-ray flexible curved panel detector 7 to receive X-ray flux to form imaging data.

Various modifications and alterations of the invention will become apparent to those skilled in the art without departing from the spirit and scope of the invention, which is defined by the accompanying claims. It should be noted that steps recited in any method claims below do not necessarily need to be performed in the order they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only, and not of limitation. The various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions, and method claims, the order in which the steps are presented herein shall not mandate that various embodiments be implemented to perform the recited functionality in the same order unless the context dictates otherwise.

Terms and phrases used in this document, and variations thereof, unless otherwise expressly stated, should be construed as open-ended as opposed to limiting. As examples of the foregoing: the term "including" should be read as meaning "including, without limitation" or the such as; the term "example" is used to provide exemplary instances of the item in the discussion, not an exhaustive or limiting list thereof; the terms "a" or "an" should be read as meaning "at least one," "one or more" or the such as; and adjectives such as "conventional," "traditional," "normal," "standard," "known" and terms of similar meaning should not be construed as limiting the item described to a given time or to an item available as of a given time, but instead should be read to encompass conventional, traditional, normal, or standard technologies that may be available or known now or at any time in the future. Hence, where this document refers to technologies that would be apparent or known to one of ordinary skill in the art, such technologies encompass those apparent or known to the skilled artisan now or at any time in the future.

What is claimed is:

1. A system to provide fast 3D radiography using X-ray flexible curved panel detector with motion compensated multiple pulsed X-ray sources, comprising:
   a primary motor stage moving freely on an arc rail with a predetermined shape;
   a primary motor coupled to said primary motor stage to control a speed of the primary motor stage;
   a plurality of secondary motor stages coupled to said primary motor stage and moved along a direction of the arc rail;
   a plurality of secondary motors, each engaging a secondary motor stage and controlling a speed of secondary motor stage;
   a plurality of X-ray sources each moved by a secondary motor stage;
   a supporting frame structure that provides housing for the primary motor stage and secondary motor stages; and
   an X-ray flexible curved panel detector to receive X-ray flux.

2. The system of claim 1, comprising:
   a predefined track; and
   a source array including multiple pulsed X-ray sources mounted on a structure in motion, wherein each of the multiple pulsed X-ray source moves simultaneously around an object on the pre-defined track at a constant speed of a group, and when an individual X-ray source tube has a speed that equals to group tube speed but in an opposite moving direction, the individual X-ray source and the X-ray flexible curved panel detector are triggered through an exposure control unit.

3. The system of claim 1, wherein a speed or a position of the primary motor stage or secondary motor stages is adjustable by software.

4. The system of claim 1, wherein the current and voltage of an X-ray source are adjustable by software.

5. The system of claim 1, wherein exposure time of X-ray source is adjustable by software.

6. The system of claim 1, wherein the X-ray source tube standstills relative to the X-ray flexible curved panel detector during an X-ray pulse trigger exposure duration.

7. The system of claim 1, wherein the result of each and accumulated analysis determines the next X-ray source and exposure condition.

8. The system of claim 1, wherein the X-ray flexible curved panel detector acquires 3D radiography image projection data with a predetermined sweep over a predetermined time period, and wherein image analysis is performed in real-time during scanning.

9. The system of claim 1, wherein each individual X-ray source moves rapidly around a static position with a predetermined distance.

10. The system of claim 1, wherein 3D X-ray radiography images are reconstructed based on each image with an angled geometry of X-ray exposure source.

11. A method of fast 3D radiography using X-ray flexible curved panel detector with motion compensated multiple pulsed X-ray sources comprising:
    positioning a primary motor stage and one or more secondary motor stages to a predetermined initial location;
    sweeping the primary motor stage at a predetermined constant speed by said primary motor;
    oscillating each of the secondary motor stages by a corresponding secondary motor with a predetermined sequence;
    electrically activating an X-ray source and an X-ray flexible curved panel detector when a secondary motor stage moves in an opposite direction to that of the primary motor stage and at a selected speed of the primary motor stage; and
    acquiring image data using the X-ray flexible curved panel detector after receiving X-ray flux from X-ray sources.

12. The method of claim 11, comprising using a stage table for a scan object.

13. The method of claim 11, comprising randomly activating the X-ray source from one of any sources in the array using a random-firing scheme.

14. The method of claim 11, comprising reconstructing 3D X-ray radiography based on each image with an angled geometry of X-ray source.

15. The method of claim 11, wherein the X-ray flexible curved panel detector acquires 3D radiography image projection data with a predetermined sweep over a predetermined time while performing image analysis in real-time during scanning.

16. The method of claim 11, comprising changing a sweep angle based on a region of interest.

17. The method of claim 11, comprising changing an X-ray source voltage input based on object density during a sweep.

18. The method of claim 11, wherein X-ray detector is coupled to a linear stage to adjust a position based on locations of X-ray sources.

19. The method of claim 11, wherein 4D imaging is performed by adding a time component to 3D spatial imaging data.

\* \* \* \* \*